(12) United States Patent
Shipp (10) Patent No.: US 10,035,617 B1
(45) Date of Patent: Jul. 31, 2018

(54) TAMPER SEAL DETECTION SYSTEM WITH CONVEYOR BELT AND METHOD OF USE

(71) Applicant: THERMO FISHER SCIENTIFIC, INC., Waltham, MA (US)

(72) Inventor: Martin Shipp, Billingshurst (GB)

(73) Assignee: Thermo Fisher Scientific, Inc., Waltham, MA (US)

( * ) Notice: Subject to any disclaimer, the term of this patent is extended or adjusted under 35 U.S.C. 154(b) by 0 days.

(21) Appl. No.: 15/421,721

(22) Filed: Feb. 1, 2017

(51) Int. Cl.
| | |
|---|---|
| *B61L 1/16* | (2006.01) |
| *B65B 57/18* | (2006.01) |
| *B65B 7/20* | (2006.01) |
| *G01V 8/10* | (2006.01) |

(52) U.S. Cl.
CPC ............... *B65B 57/18* (2013.01); *B65B 7/20* (2013.01); *G01V 8/10* (2013.01)

(58) Field of Classification Search
CPC ........... G06M 7/04; G06M 1/08; G06M 1/086
USPC ...................................................... 235/98 R
See application file for complete search history.

(56) References Cited

U.S. PATENT DOCUMENTS

| | | | | |
|---|---|---|---|---|
| 6,641,042 | B1* | 11/2003 | Pierenkemper | G06K 7/0008 235/461 |
| 6,896,185 | B2* | 5/2005 | Uhl | G06K 7/10792 235/454 |
| 7,215,363 | B2* | 5/2007 | Stamm | B07C 3/14 348/139 |
| 8,248,620 | B2* | 8/2012 | Wicks | G01B 11/002 340/568.1 |
| 2007/0296963 | A1* | 12/2007 | Parker | G01N 21/55 356/240.1 |
| 2009/0009192 | A1 | 1/2009 | Farrelly et al. | |
| 2010/0013500 | A1 | 1/2010 | Maher et al. | |
| 2013/0008962 | A1* | 1/2013 | Anand | G06K 7/10 235/454 |
| 2013/0161159 | A1 | 6/2013 | Fisher et al. | |
| 2015/0241360 | A1* | 8/2015 | Niemela | G01N 21/95 356/369 |

FOREIGN PATENT DOCUMENTS

| | | |
|---|---|---|
| EP | 1 486 925 A2 | 12/2004 |
| EP | 2 508 862 A1 | 10/2012 |
| JP | 2007-71568 A | 3/2007 |

* cited by examiner

*Primary Examiner* — Ahshik Kim
(74) *Attorney, Agent, or Firm* — Workman Nydegger (57) ABSTRACT

A method for detecting sealing stickers on a packaging box includes placing a first packaging box onto a conveyor belt of a conveyor belt system at an inspection zone, the first packaging box having a first sealing sticker thereon that at least partially seals the first packaging box closed; and activating a first optical sensor to detect whether the first sealing sticker is located on a first side of the first packaging box while the packaging box is in the inspection zone.

23 Claims, 6 Drawing Sheets

FIG. 8 the sealing sticker is manually placed on the outside of the box so as to extend between the lid and the body of the box, thereby fixing the lid closed and sealing the contents therein. The unbroken sealing sticker indicates that the box has not been opened following sealing of the product therein. The box can also be marked with one or more labels that include an identification number or other information associated with the included product. However, such identifying information is keyed to a reference list and is only useful in identifying the product in combination with that list. Accordingly, the box may also lack any direct, product-identifying marks or labels to ensure fidelity of the blinded study.
TAMPER SEAL DETECTION SYSTEM WITH CONVEYOR BELT AND METHOD OF USE

CROSS-REFERENCE TO RELATED APPLICATIONS

Not applicable.

BACKGROUND OF THE INVENTION

1. The Field of the Invention

The present invention relates to tamper seal detection systems used in inspecting the packaging of drugs for blinded clinical trials and methods of using such systems.

2. The Relevant Technology

Clinical trials for many pharmaceutical drugs require that a drug and a placebo be delivered and administered in a blinded study. As part of the blinded clinical trial protocols, the drug and placebo are placed in separate unmarked containers. Accordingly, the administering technician and recipient are blind as to the identity of the product, the concentration thereof, or other characteristic being studied that may otherwise be reported on the retail label of the drug container.

To facilitate transport and delivery of the drug/placebo, the unmarked containers can be sealed in a box. For instance, an unmarked dosage vial or tube can be placed in a box having a lid that can be folded over to close the box. Once the lid is closed, a sealing sticker is manually placed on the outside of the box so as to extend between the lid and the body of the box, thereby fixing the lid closed and sealing the contents therein. The unbroken sealing sticker indicates that the box has not been opened following sealing of the product therein. The box can also be marked with one or more labels that include an identification number or other information associated with the included product. However, such identifying information is keyed to a reference list and is only useful in identifying the product in combination with that list. Accordingly, the box may also lack any direct, product-identifying marks or labels to ensure fidelity of the blinded study.

The packaging of the drug/placebo is typically performed in large batches. For example, a single continuous run may package desired dosages of drugs and/or placebos within 4,000 different boxes. Packaging protocols for blinded clinical trials require that an inspection process be used to ensure that sealing sticker(s) are applied to every box. One inspection process comprises counting the actual number of sealing stickers used and comparing it to the number of stickers that should have been used. For example, some boxes require two stickers, one on the top and one on the bottom, to properly seal the box. Thus, if 4,000 boxes are packaged, 8,000 stickers should have been used. The problem with this approach, however, is that if the sticker count is off by one, all of the 4,000 boxes may need to be inspected to ensure that all of the boxes are properly sealed and determine why the count is off. As can be appreciated, such an inspection can be labor intensive, time consuming, and potentially subject to human error. Similar problems also exist with other inspection processes.

Accordingly, what is needed in the art are systems and methods for more accurately and efficiently inspecting boxes containing drugs or placebos used in blinded clinical studies to ensure that they are properly sealed.

SUMMARY OF THE INVENTION

In one independent embodiment of the invention, a method for detecting sealing stickers on a packaging box can include:
   placing a first packaging box onto a conveyor belt of a conveyor belt system at an inspection zone, the first packaging box having a first sealing sticker thereon that at least partially seals the first packaging box closed; and
   activating a first optical sensor to detect whether the first sealing sticker is located on a first side of the first packaging box while the packaging box is in the inspection zone.

The conveyor belt of the conveyor belt system can be automatically moved a predefined distance so that the first packaging box is moved out of the inspection zone if the first optical sensor detects that the first sealing sticker is located on the first side of the first packaging box.

The conveyor belt of the conveyor belt system can be not moved if the first optical sensor detects that the first sealing sticker is not located on the first side of the first packaging box until after the first packaging box is removed from the conveyor belt.

A second optical sensor can be activated to detect whether a second sealing sticker is located on a second side of the first packaging box while the first packaging box is located on the conveyor belt within the inspection zone.

The conveyor belt of the conveyor belt system can be automatically moved a predefined distance so that the first packaging box is moved out of the inspection zone if the first optical sensor detects that the first sealing sticker is located on the first side of the first packaging box and the second optical sensor detects the second sealing sticker is located on a second side of the first packaging box.

A first packaging box can be placed onto the conveyor belt so that that first packaging box butts against a rear guide rail on which the first optical sensor is attached and butts against a side guide rail on which the second optical sensor is attached.

A second packaging box can be placed on the conveyor belt in the inspection zone after the conveyor belt has moved the predefined distance.

Prior to the step of inserting the first packaging box, the method can include:
   inserting a blinded trial product into a compartment of the first packaging box;
   folding the first packaging box into a closed position; and
   applying the first sealing sticker to the packaging box so as to at least partially seal the packaging box closed.

The blinded trial product can include an active drug product, a comparative drug product, a control drug product, or a placebo product.

The position of the first optical sensor can be manually adjusted before placing a first packaging box onto the belt.

The optical sensor can be adjusted in two dimensions.

The electronic controller can be in electrical communication with the first optical sensor, the electronic controller being programed to generate a notice signal when the first optical sensor detects that the first sealing sticker is located on a first side of the first packaging box.

The electronic controller can be is in electrical communication with the first optical sensor, the electronic controller being programed to generate a notice signal when the first optical sensor detects that the first sealing sticker is not located on a first side of the first packaging box.

The first optical sensor can detect the first sealing sticker based on the color, size, shape, or orientation of the first sealing sticker or indicia disposed on the first sealing sticker.

The first optical sensor can detect whether the first sealing sticker is located within a specific predefined area on the first side of the packaging box.

The first optical sensor can detect whether the first sealing sticker is orientated in a specific predefined orientation on the first side of the packaging box.

The first optical sensor can be a luminescence sensor or vision sensor.

A first proximity sensor can be activated to detect whether the first packing box is in the inspection zone.

The first proximity sensor can be a photoelectric proximity sensor. The photoelectric proximity sensor can be of the reflective, thrubeam, or retroreflective type.

The step of placing the first packaging box onto the conveyor belt can include:
  adjusting a lateral position of a second side guide rail; and
  placing the first packaging box onto the conveyor belt so that the packing box is disposed between a first side guide rail and the second side guide rail.

In another independent embodiment of the present invention, a tamper seal detection system for detecting a sealing sticker on a packaging box can include:
  a conveyor belt system having a movable conveyor belt with an inspection zone that is configured to receive a packaging box having one or more sealing stickers thereon;
  a rear guide rail and a first side guide rail disposed adjacent to the conveyor belt of the conveyor belt system; and
  a first sensor secured to the rear guide rail or the first side guide rail and being configured to detect the presence of a first sealing sticker located on the packaging box when the packaging box is received on the conveyor belt within the inspection zone.

A second sensor can be secured to the other of the rear guide rail or the first side guide rail and being configured to detect the presence of a second sealing sticker located on the packaging box when the packaging box is received on the conveyor belt within the inspection zone.

The first sensor can be adjustable mounted on the housing so that the first sensor can be moved in at least two dimensions.

The rear guide rail can be disposed orthogonal to the first side guide rail.

A second side guide rail can be disposed parallel to the first side guide rail and can be moved laterally.

An electronic controller can be in electrical communication with the conveyor belt system and the first sensor.

A notice generator can be in electrical communication with the electronic controller.

The notice generator can include a light source or sound generator.

The tamper seal detection system can also further include:
  an electronic controller in electrical communication with the conveyor belt system and the first sensor, the electronic controller being programmed to perform the following functions:
  activating the first sensor to determine whether the first sealing sticker is located on a first side of the packaging box that is located within the inspection zone; and
  sending a signal to the conveyor belt system which causes the conveyor belt system to move the conveyor belt a predetermined distance.

The first sensor can detect the shape, size, color, location, or orientation of a sealing sticker.

A blinded trial product can be disposed within the packaging box.

The first sensor can be an optical sensor.

The first sensor can be a luminescence sensor or a vision sensor.

A first proximity sensor can be disposed on the rear guide rail or the first side guide rail, the proximity sensor being capable of detecting whether a packaging box is located within the inspection zone.

The first proximity sensor can be a photoelectric proximity sensor. The photoelectric proximity sensor can be of the reflective, thrubeam, or retroreflective type.

A second proximity sensor can be disposed on the first side guide rail at a location spaced apart from the inspection zone.

A third sensor located vertically above the inspection zone.

It is appreciated that features, elements, methods steps and other aspects set forth under each of the above independent embodiments of the present invention can be combined with the other independent embodiment.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Before describing the present disclosure in detail, it is to be understood that this disclosure is not limited to parameters of the particularly exemplified systems, methods, apparatus, products, processes, and/or kits, which may, of course, vary. It is also to be understood that the terminology used herein is only for the purpose of describing particular embodiments of the present disclosure, and is not necessarily intended to limit the scope of the disclosure in any particular manner. Thus, while the present disclosure will be described in detail with reference to specific embodiments, features, aspects, configurations, etc., the descriptions are illustrative and are not to be construed as limiting the scope of the claimed invention. Various modifications can be made to the illustrated embodiments, features, aspects, configurations, etc. without departing from the spirit and scope of the invention as defined by the claims. Thus, while various aspects and embodiments have been disclosed herein, other aspects and embodiments are contemplated.

Unless defined otherwise, all technical and scientific terms used herein have the same meaning as commonly understood by one of ordinary skill in the art to which the present disclosure pertains. While a number of methods and materials similar or equivalent to those described herein can be used in the practice of the present disclosure, only certain exemplary materials and methods are described herein.

Various aspects of the present disclosure, including devices, systems, methods, etc., may be illustrated with reference to one or more exemplary embodiments or implementations. As used herein, the terms "embodiment," "alternative embodiment" and/or "exemplary implementation" means "serving as an example, instance, or illustration," and should not necessarily be construed as preferred or advantageous over other embodiments or implementations disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

It will be noted that, as used in this specification and the appended claims, the singular forms "a," "an" and "the" include plural referents unless the content clearly dictates otherwise. Thus, for example, reference to a "sensor" includes one, two, or more sensors.

As used throughout this application the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

Various aspects of the present disclosure can be illustrated by describing components that are coupled, attached, connected, and/or joined together. As used herein, the terms "coupled", "attached", "connected," and/or "joined" are used to indicate either a direct connection between two components or, where appropriate, an indirect connection to one another through intervening or intermediate components. In contrast, when a component is referred to as being "directly coupled", "directly attached", "directly connected," and/or "directly joined" to another component, no intervening elements are present or contemplated. Thus, as used herein, the terms "connection," "connected," and the like do not necessarily imply direct contact between the two or more elements. In addition, components that are coupled, attached, connected, and/or joined together are not necessarily (reversibly or permanently) secured to one another. For instance, coupling, attaching, connecting, and/or joining can comprise placing, positioning, and/or disposing the components together or otherwise adjacent in some implementations.

As used herein, directional and/or arbitrary terms, such as "top," "bottom," "front," "back," "left," "right," "up," "down," "upper," "lower," "inner," "outer," "internal," "external," "interior," "exterior," "proximal," "distal" and the like can be used solely to indicate relative directions and/or orientations and may not otherwise be intended to limit the scope of the disclosure, including the specification, invention, and/or claims.

Where possible, like numbering of elements have been used in various figures. In addition, similar elements and/or elements having similar functions may be designated by similar numbering (e.g., element "10" and element "210.") Furthermore, alternative configurations of a particular element may each include separate letters appended to the element number. Accordingly, an appended letter can be used to designate an alternative design, structure, function, implementation, and/or embodiment of an element or feature without an appended letter. Similarly, multiple instances of an element and or sub-elements of a parent element may each include separate letters appended to the element number. In each case, the element label may be used without an appended letter to generally refer to instances of the element or any one of the alternative elements. Element labels including an appended letter can be used to refer to a specific instance of the element or to distinguish or draw attention to multiple uses of the element. However, element labels including an appended letter are not meant to be limited to the specific and/or particular embodiment(s) in which they are illustrated. In other words, reference to a specific feature in relation to one embodiment should not be construed as being limited to applications only within said embodiment.

It will also be appreciated that where a range of values (e.g., less than, greater than, at least, and/or up to a certain value, and/or between two recited values) is disclosed or recited, any specific value or range of values falling within the disclosed range of values is likewise disclosed and contemplated herein. Thus, disclosure of an illustrative measurement or distance less than or equal to about 10 units or between 0 and 10 units includes, illustratively, a specific disclosure of: (i) a measurement of 9 units, 5 units, 1 units, or any other value between 0 and 10 units, including 0 units and/or 10 units; and/or (ii) a measurement between 9 units and 1 units, between 8 units and 2 units, between 6 units and 4 units, and/or any other range of values between 0 and 10 units.

It is also noted that systems, methods, apparatus, devices, products, processes, compositions, and/or kits, etc., according to certain embodiments of the present invention may include, incorporate, or otherwise comprise properties, features, aspects, steps, components, members, and/or elements described in other embodiments disclosed and/or described herein. Thus, reference to a specific feature, aspect, steps, component, member, element, etc. in relation to one embodiment should not be construed as being limited to applications only within said embodiment. In addition, reference to a specific benefit, advantage, problem, solution, method of use, etc. in relation to one embodiment should not be construed as being limited to applications only within said embodiment.

The headings used herein are for organizational purposes only and are not meant to be used to limit the scope of the description or the claims. To facilitate understanding, like reference numerals have been used, where possible, to designate like elements common to the figures.

The present invention relates to tamper seal detection systems that can be used as part of an inspection process to determine, in part, whether sealing stickers are located and/or properly positioned on packaging boxes containing blinded trial product used in blinded trials. In other embodiments, the tamper seal detection systems can be used to determine whether sealing stickers are located and/or properly positioned on packaging boxes containing products not used in blinded trials but where it is desired to inspect the proper application of sealing stickers. Furthermore, the tamper seal detection systems can also be used to determine whether select labels are applied to or select indicia is printed on packaging boxes, whether or not used for blinded trials, and can process and store information from such labels or indicia.

Figure 1:
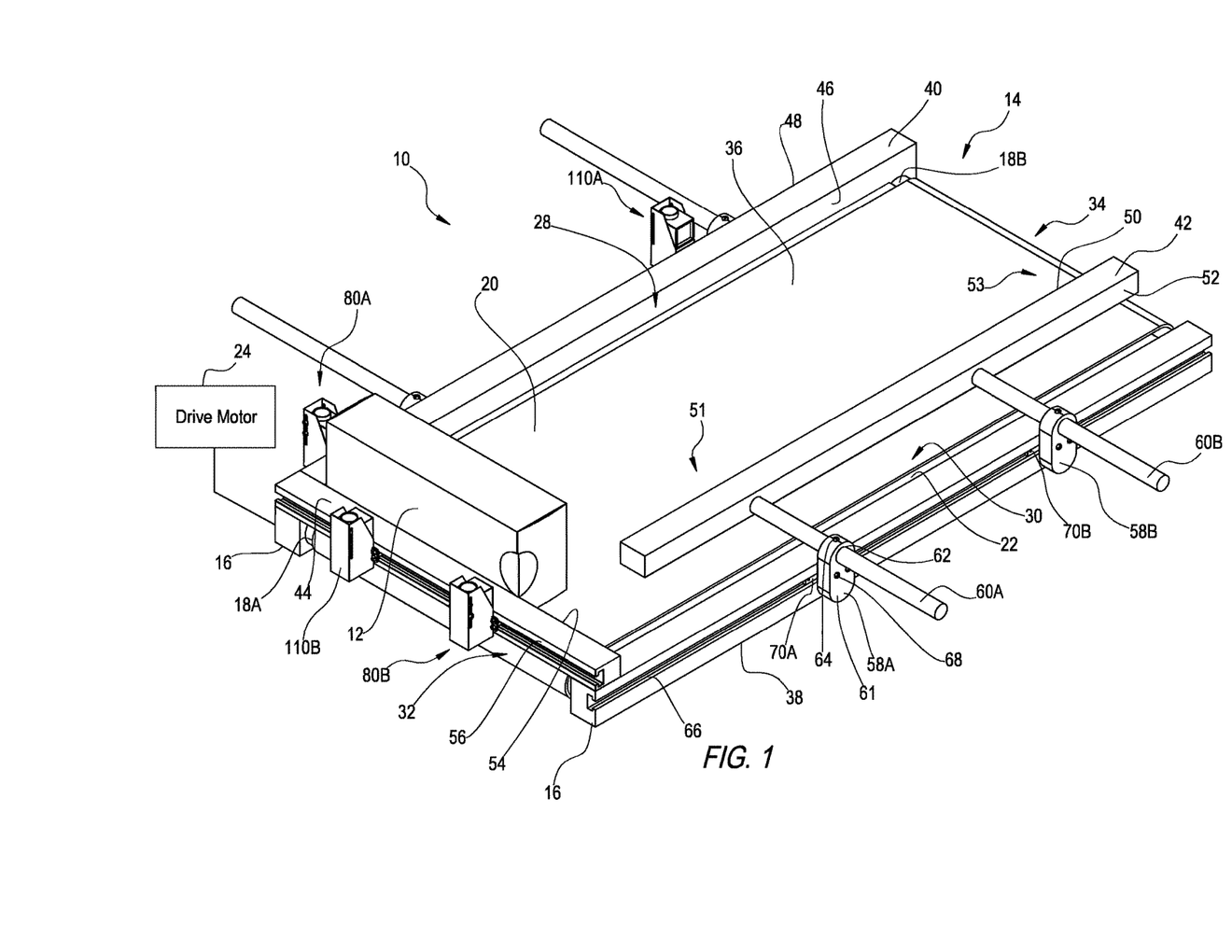
FIG. 1 is a right front perspective view of the tamper seal detection system showing a packaging box disposed thereon.

By way of example and not by limitation, depicted in FIG. 1 is one embodiment of a tamper seal detection system 10 incorporating features of the present invention and used to detect sealing stickers on a packaging box 12. Tamper seal detection system 10 comprises a conveyor belt system 14 that includes a frame 16, a pair of spaced apart roller 18A and 18B rotatably mounted to frame 16, and a looped convey belt 20 that spans between and is looped around rollers 18A and 18B. Conveyor belt 20 is tensioned between rollers 18A and 18B so that as roller 18A is rotated, conveyor belt 20 rotates in a continuous loop between and around rollers 18A and 18B.

Conveyor belt system 14 also includes a platform 22 supported by frame 16. Platform 22 is disposed between rollers 18A and 18B and is encircled by conveyor belt 20 so that conveyor belt 20 passes over platform 22 as conveyor belt travels between rollers 18A and 18B. The function of platform 22 is to support conveyor belt 20 as an item, such as one or more packaging boxes 12, travels along the length of conveyor belt 20 between rollers 18A and 18B. Platform 22 can comprise a flat panel, a plurality of rollers a combination of the foregoing or other structures that can support conveyor belt 20 as conveyor belt 20 moves over platform 22. Finally, conveyor belt system 14 also includes a drive motor 24 that mechanically engages with roller 18A, such as through direct drive, gear, belt, chain, cable or the like, so that drive motor 24 can rotate roller 18A at select time intervals and at select speeds. In turn, the rotation of roller 18A facilitates the corresponding rotation of conveyor belt 20.

In general, conveyor belt 20 is defined as having a first side 28 and an opposing second side 30 that extend between a first end 32 (where roller 18A is located) and an opposing second end 34 (where roller 18B is located). Conveyor belt 20 also has a top surface 36 and an opposing bottom surface 38.

Tamper seal detection system 10 also includes a first side guide rail 40, a second side guide rail 42 and a rear guide rail 44 that are each disposed above or project above top surface 36 of conveyor belt 20. First side guide rail 40 is elongated and has a flat inside face 46 and an opposing outside face 48 that extend between opposing ends. First side guide rail 40 is disposed at or toward first side 28 of conveyor belt 20 with inside face 46, and typically the longitudinal axis of first side guide rail 40, being disposed in parallel alignment with conveyor belt 20. First side guide rail 40 can extend the full length or a portion of the length of conveyor belt 20.

Second side guide rail 42 is elongated and has a flat inside face 50 and an opposing outside face 52 that extend between a first end 51 and an opposing second end 53. Second side guide rail 42 is disposed at or toward second side 30 of conveyor belt 20 with inside face 50, and typically the longitudinal axis of second side guide rail 42, being disposed in parallel alignment with conveyor belt 20. Second side guide rail 42 can extend the full length or a portion of the length of conveyor belt 20. Rear guide rail 44 is elongated and has a flat inside face 54 and an opposing outside face 56 that extend between opposing ends. Rear guide rail 44 is disposed at or toward first end 32 of conveyor belt 20 with inside face 54, and typically the longitudinal axis of rear guide rail 44, being disposed perpendicular to conveyor belt 20. Rear guide rail 44 can extend the full width or a portion of the width of conveyor belt 20.

To accommodate different sizes of packaging boxes 12, at least one of first side guide rail 40 or second side guide rail 42 can be adjustable mounted so that the lateral position of guide rails 40 and 42 across the width of conveyor belt 20 can be selectively adjusted. For example, spaced apart clamps 58A and 58B are secured to frame 16 on second side 30 of conveyor belt 20 so as to project above top surface 36. A pair of spaced apart staves 60A and 60B project from second side guide rail 42, such as from outside face 52, and couple with clamps 58A and 58B, respectively. By adjusting the position of where clamps 58A and 58B secure along the length of staves 60A and 60B, the location of second side guide rail 42 across the width of conveyor belt 20 can be adjusted. That is, second side guide rail 42 can be moved closer to first side guide rail 40 so that the distance between inside faces 46 and 50 decreases for smaller packaging boxes 12 or second side guide rail 42 can be moved farther away first side guide rail 40 so that the distance between inside faces 46 and 50 increases for larger packaging boxes 12.

It is appreciated that clamps 58 can come in a variety of different configurations with a number of different mechanisms for releasably attaching to staves 60. In the depicted embodiment, each clamp has a body 61 through which a hole 62 passes. A fastener 64, such as a screw, threads into body 61 and can extend into hole 62. Staves 60 pass through holes 62 and are releasably secured therein by fasteners 64. In alternative embodiments, it is appreciated that clamps 58 can be formed with a synch, cam, spring biased arm(s), cleat, vise or any other mechanism that can releasably secure staves 60.

In the depicted embodiment, the position of second side guide rail 42 can also be adjusted longitudinally along the length of conveyor belt 20. A T-shaped channel 66 is formed along the length of frame 16. Fasteners 68 are used to secure clamp body 61 to frame 16 by passing through clamp body 61 and threading into stops 70 that are slidably captured within channel 66. When fasteners 68 are loosened, stops 70 are released and clamps 58 can freely slide laterally along the length of frame 16, thereby enabling the movement of second side guide rail 42 along the length of conveyor belt 20. In contrast, as fasteners 68 are tightened, stops 70 bias against frame 16, thereby locking clamps 58 to frame 16. Again, a variety of different releasing structures can be used to releasably secure clamps 58 to frame 16.

Figure 2:
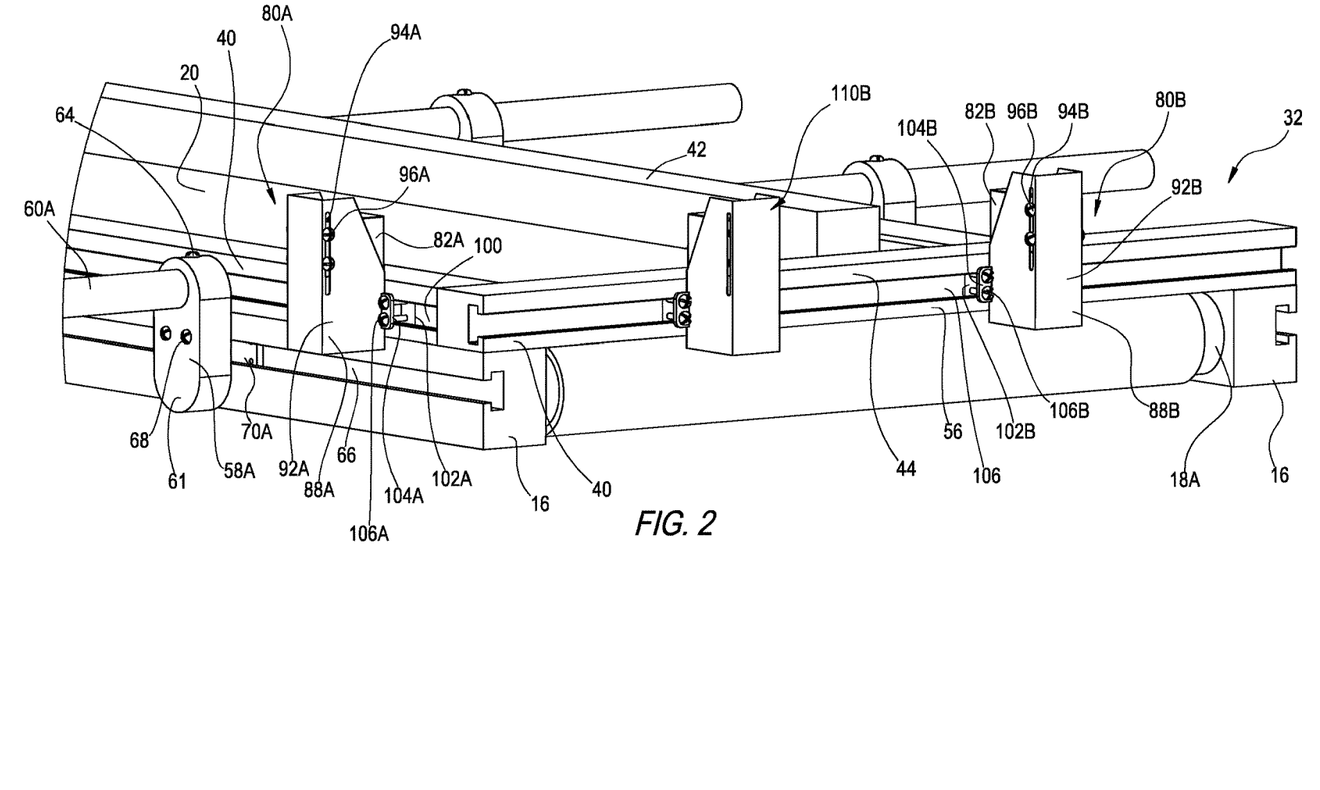
FIG. 2 is a left front perspective view of the tamper seal detection system shown in FIG. 1.

In one embodiment, second side guide rail 42 may be adjustable laterally and/or longitudinally along conveyor belt 20, as discussed above, while first side guide rail 40 may be permanently fixed to frame 16. However, in another embodiment, first side guide rail 40 may be adjustable laterally and/or longitudinally along conveyor belt 20 using the same clamping structure as discussed above with regard to second side guide rail 42. For example, as depicted in FIG. 2, clamps 58 and staves 60, or the alternatives thereof as discussed above, can also be used for movably securing first side guide rail 40 to frame 16.

Rear guide rail 44 spans between portions of frame 16 on opposing sides of conveyor belt 20. Although rear guide rail 44 is typically positioned at first end 32 of conveyor belt 20, rear guide rail 44 can be positioned closer to second end 34, such as centrally on conveyor belt 20. Rear guide rail 44 can be securely fixed to frame 16 or clamps 58 and staves 60, or the alternatives thereof as discussed above, can again be used for movably securing rear guide rail 44 to frame 16.

As depicted in FIG. 1, a sensor assembly 80A is movably secured to first side guide rail 40 while a sensor assembly 80B is movably secured to rear guide rail 44. As discussed below in greater detail, sensor assemblies 80 can be programmed to detect the presence of sealing stickers located on packaging box 12 when packaging box 12 is supported on conveyor belt 20. FIG. 1 also shows a sensor assembly 110A that is movably secured to first side guide rail 40 while a sensor assembly 110B is movably secured to rear guide rail 44. As discussed below in greater detail, sensor assemblies 110 can be programmed to detect the presence of packaging boxes 12 when packaging boxes 12 are supported on conveyor belt 20.

Figure 6:
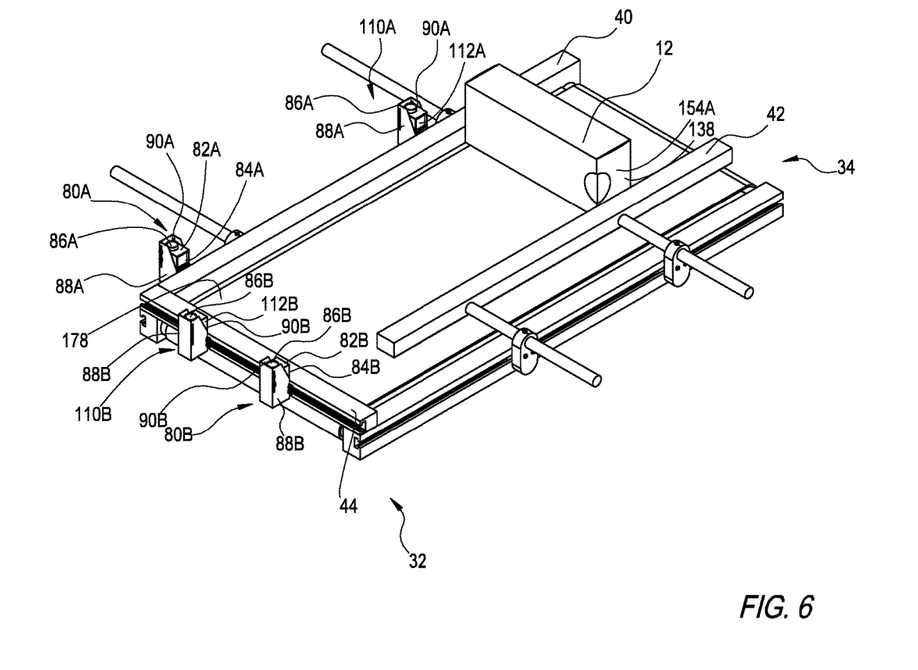
FIG. 6 is a perspective view of the tamper seal detection system shown in FIG. 5 with the packaging box in a second position.

As perhaps best depicted in FIG. 6, sensor assembly 80A comprises an optical sensor 82A having a front face with an optical eye 84A formed thereon. Optical sensor 82A can be used to detect sealing stickers as discussed below. In one embodiment, optical sensor 82A can comprise a luminescence sensor that emits UV light. Luminescence sensors detect visible and non-visible marks that illuminate when using ultraviolet (UV) light. Fluorescent material and marks are reliably detected independently of their pattern, colors or surface conditions on any material. Luminescence sensors emit UV light with a wave length of approximately 375 nm. Fluorescent substances convert the UV light into long-wave visible light, which is then received and evaluated by the luminescence sensor.

One specific example of luminescence sensors that can be used in the present invention are the LR-W Series, full-spectrum sensors available from Keyence. In other embodiments, optical sensor 82A can comprise a vision sensor or vision inspection system which grab an image and exploit any of a number of pattern matching tools to form a judgement on the presence of the sealing sticker. Other types of optical sensors that can be programmed to perform one or more of the functions described herein can also be used. Optical sensor 82A has a top face having a light source 86A formed thereon. Light source 86A can comprise a light emitting diode (LED) or other light source.

Sensor assembly 80A also includes a housing 88A having a compartment 90A in which optical sensor 82A is received and secured. Sensor assembly 80A is configured so that the position of optical sensor 82A can be adjusted both vertically and horizontally. For example, as depicted in FIG. 2, housing 88A has a vertically extending side surface 92A having an elongated, vertically extending slot 94A extending therethrough. Fasteners 96A pass through slot 94A and engage optical sensor 82A. Accordingly, by loosening fasteners 96A, optical sensor 82A can be freely slid vertically up or down relative to housing 88A. When optical sensor 82A is in the desired position, fasteners 96A can be tighten which rigidly secures optical sensor 82A to housing 88A.

Furthermore, outer face 48 of first side guide rail 40 has a T-shaped slot 100 extending longitudinally along the length thereof. A stop 102A is slidably captured within slot 100. Housing 88A includes a mount 104A having fasteners 106A that pass therethrough and engage stop 102B. Accordingly, by loosening fasteners 106A, the entire sensor assembly 80A and stop 102B can freely slide horizontally along the length of first side guide rail 40. When optical sensor 82A is in the desired horizontal position, fasteners 106A can be tighten which rigidly secure sensor assembly 80A to first side guide rail 40A. Accordingly, by using the above configurations, the position of optical sensor 82A can be selectively adjusted vertically and horizontally relative to stationary conveyer belt 20. The above is only one example of configurations for moving optical sensor 82A in two dimensions. It is appreciated that a variety of other configurations could also be used.

As also depicted in FIG. 2, outside face 56 of rear guide rail 44 has a T-shaped slot extending along the length thereof. A stop 102B is slidably captured within slot 100. Sensor assembly 80B has the same configuration as sensor assembly 80A. As such, like elements between sensor assemblies 80A and 80B are identified by like reference characters except that the reference characters of sensor assembly 80B are associated with the letter "B." In the same way that the position of optical sensor 82A can be freely adjusted vertically and horizontally, optical sensor 82B can also be freely adjusted both vertically and horizontally. That is, as depicted in FIG. 2, by loosening fasteners 96B, optical sensor 82B can be vertically adjusted and by loosening fasteners 106B which engage stop 102B, sensor assembly 80B, which includes optical sensor 82B, can be horizontally adjusted. Again, alternative mechanisms can be used to selectively adjust the vertical and horizontal position of optical sensor 82B.

Returning to FIG. 6, sensor assembly 110A is substantially identical to sensor assembly 80A except that optical sensor 82A, which is used detect sealing stickers, is replaced with an optical sensor 112A that only needs to be capable to detecting the presence of packaging box 12. In one embodiment, optical sensors 112A can comprise a proximity sensor and, more specifically, a photoelectric proximity sensor. The photoelectric proximity sensor can be of the reflective, thrubeam, or retroreflective type. One specific example of a photoelectric proximity sensor that can be used in the present invention is the WT150-P460 sensor available from Sick AG. In other embodiments, optical sensor 112A can comprise the same sensors used for optical sensor 82A, discussed above. For example, optical sensor 112A can comprise a luminescence sensor or a vision sensor. Other types of optical sensors that can be programmed to perform the functions described herein can also be used.

Like elements between sensor assemblies 80A and 110A are identified by like reference characters. Accordingly, optical sensor 112A has a top face having light source 86A formed thereon. Sensor assembly 110A also includes housing 88A having compartment 90A in which optical sensor 112A is received and secured. Sensor assembly 110A is attached to first side guide rail 40 in the same way as sensor assembly 80A. As such, the position of optical sensor 112A can be selectively adjusted both vertically and horizontally as previously discussed with regard to optical sensor 82A.

Sensor assembly 110B is likewise substantially identical to sensor assembly 80B except that optical sensor 82B, which is used detect sealing stickers, is replaced with an optical sensor 112B that only needs to be capable to detecting the presence of packaging box 12. Optical sensor 112B can be the same as optical sensor 112A as discussed above. Like elements between sensor assemblies 80B and 110B are identified by like reference characters. Accordingly, optical sensor 112B has a top face having light source 86B formed thereon. Sensor assembly 110B also includes housing 88B having compartment 90B in which optical sensor 112B is received and secured. Sensor assembly 110B is attached to rear guide rail 44 in the same way as sensor assembly 80B. As such, the position of optical sensor 112B can be selectively adjusted both vertically and horizontally as previously discussed with regard to optical sensor 82B. In contrast to being attached to rear guide rail 44, sensor assembly 110B could be attached to first side guide rail 40. In another embodiment, a first sensor assembly 110B could be attached to rear guide rail 44 while a second sensor assembly 110B can be attached to first side guide rail 40.

Depicted in FIG. 1 is a perspective view of packaging box 12. It is appreciated that packaging box 12 can come in a variety of different sizes, shapes and configurations. Packaging box 12 can be comprised of and/or formed from a foldable sheet of material. Specifically, packaging box 12 can be formed as a template that has been cut, such as through a die press or otherwise formed, so that it can be folded and secured into the box shape configuration. Packaging box 12 can be comprised of a foldable sheet of material that typically retains a crease when folded. For example, the sheet can comprise a paper-based material, such as paper, cardstock, paperboard or cardboard. In other embodiments, the sheet can be comprised of a synthetic, plastic, or other material (e.g., adapted to retain a crease when folded). The sheet can comprise a single, continuous, unitary structure; a composite; a laminate; an extrusion; or a base sheet having a coating on one or both opposing sides thereof. Packaging box 12 can also be formed of two or more sheets that are connected together, such as through an adhesive or welding.

The material for packaging box 12 can have a thickness suitable for various different embodiments. For instance, the material can have a thickness of up to, at least, or about 0.25 mm, 0.5 mm, 1 mm, 1.5 mm, 2 mm, 2.5 mm, 3 mm, and/or 5 mm or between any two of the foregoing. Thicknesses less than 0.25 mm or greater than 5 mm are also contemplated herein. In addition, various components of packaging box 12 may have varying or different thicknesses in some embodiments.

As illustrated in FIG. 1, the final fully assembled and closed packaging box 12 can have a box shaped configuration, i.e., a parallelepiped hexahedron, having square or rectangular panels. Accordingly, the panels of packaging box 12 can be disposed at successive right angles one to another. In other embodiments, packaging box 12 can have other hexahedron or polyhedron configurations or other three dimensional configurations such as cylindrical or conical. As such, an encircling side wall of packaging box 12, discussed below, can have a circular, oval, or other geometric transverse cross sectional configurations.

Figure 3:
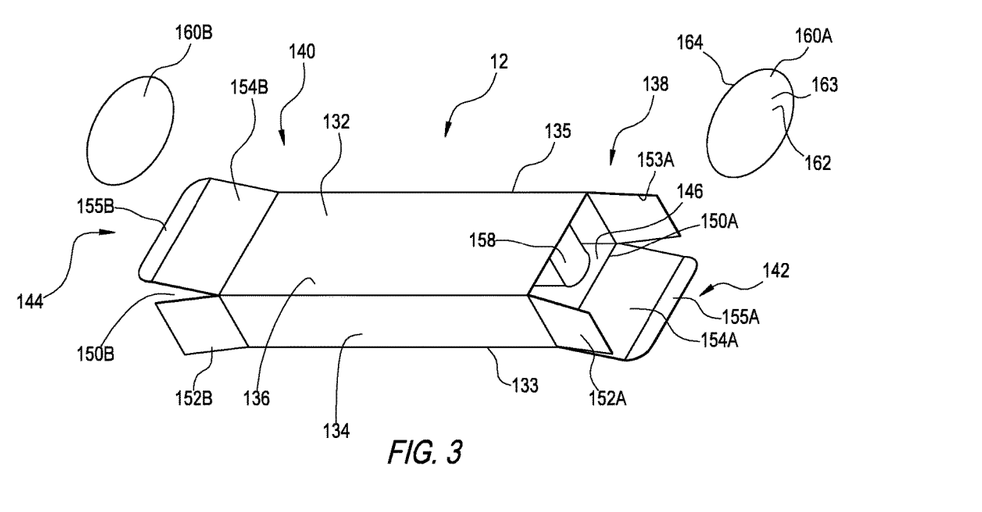
FIG. 3 is a perspective view of the packaging box shown in FIG. 1 in an open position.

As depicted in FIG. 3, packaging box 12 has a front panel 132, an opposing rear panel 133, and opposing side panels 134 and 135 extending between the opposing ends thereof. Panels 132-135 combine to form a continuous encircling sidewall 136 that is folded at the corners. Although not required, in this embodiment sidewall 136 is elongated and extends to opposing ends 138 and 140. Packaging box 12 also has a first end closure 142 located a first end 138 and a second end closure 144 located at second end 140.

Figure 4:
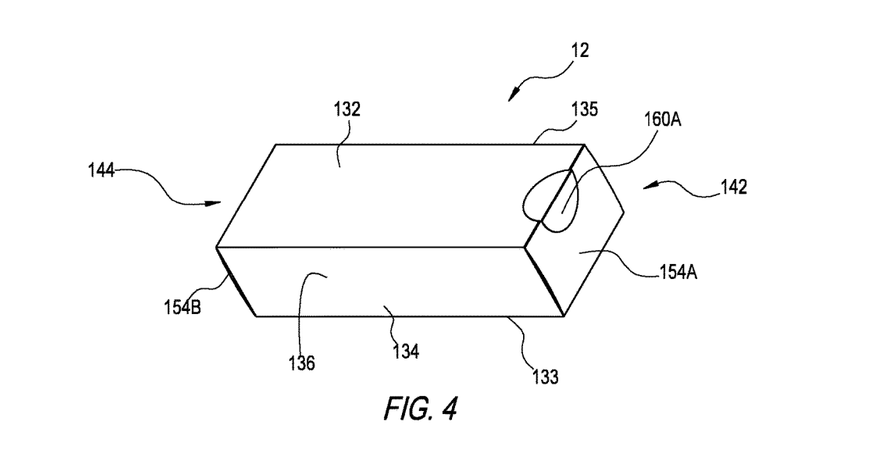
FIG. 4 is a perspective view of the packaging box shown in FIG. 3 in a closed position.

End closures 142 and 144 will often comprise a plurality of separate panels that interlock, overlap and/or fold together. For example, packaging box 12 has an interior surface 146 that bounds a compartment 148. Compartment 148 has an opening 150A at end 138 and an opening 150B at end 140. Openings 150A and 150B are bounded by the terminal edges of panels 132-135 at the opposing ends thereof. End closure 142 comprises dust flaps 152A and 153A that project from the terminal edge of side panels 134 and 135, respectively and can inwardly fold to extend over a portion of opening 150A. End closure 142 also includes a closure panel 154A that projects from a terminal edge of rear panel 133 and a tuck flap 155A that extends from a free end of closure panel 154A. To close opening 150A, dust flaps 152A and 154A are initially folded inwardly over opening 150A. Closure panel 154A is then folded over opening 150A and extends to front panel 132. Tuck flap 155 is slid into opening 150A so as to be captured between dust flaps 152A/154A and front panel 132. Tuck flap 155A assists in keeping closure panel 154A in the closed position, as shown in FIG. 4, where opening 150A is covered.

Continuing with FIG. 3, end closure 144 located at second end 140 to close opening 150B has the same elements and operates in the same manner as end closure 142. As such, like elements between end closures 142 and 144 are identified by like reference characters except that the elements for end closure 144 are associated with the letter "B." The one difference between end closures 142 and 144 is that closure panel 154B of end closure 144 projects from a terminal edge of front panel 132 rather than rear panel 133. However, in other embodiments, closure panel 154B could again project from rear panel 133.

Prior to closing end closures 142 and 144, a blinded trial product 158 or other desired item is disposed within compartment 148. In at least one embodiment, blinded trial product 158 can comprise one or more different products (e.g., clinical trial materials (CTM)). For example, blinded trial product 158 can comprise a test product that can comprise an active drug product, a comparative drug product, a control drug product, a placebo product, or one or more combinations of the foregoing. Furthermore, in different packaging boxes 12 the active drug product, comparative drug product, control drug product, and/or placebo product can be provided in different quantities, volumes, concentrations, strengths, types (i.e., pill, ointment, liquid, injection, etc.) or combinations of the foregoing. Furthermore, in at least one embodiment, blinded trial product 158 can include multiple dosages or concentrations of one or more different blinded trial products 158. Accordingly, blinded trial product 158 can comprise a plurality of different containers and different container types being placed in the same or different packaging boxes 12. Depending on the form of the drug being tested, the foregoing products may be housed in pill bottles, syringes, vials, tubes or other conventional containers.

Blinded trial product 158 can also comprise one or more support products such as antiseptics, band aids, swabs, gauze, tape, instructions, disposal containers or any other accessories that may be used or associated with the drug being tested. The blinded trial product 158 can be held securely within compartment 148 by way of packaging. In some embodiments, "blinded trial products" (or similar terms) can include any clinical trial material (CTM) and does not need to be limited to blinded materials or materials used in blinded trials or studies or components used therein. In other embodiments, any product or combination of products can be housed within packaging box 12.

After closure panels 154A and 154B are moved to the closed position so that openings 152A and 152B are closed, sealing stickers 160A and 160B, as shown in FIGS. 3 and 4, are applied so as to extend between closure panel 154A and front panel 132 and between closure panel 154B and rear panel 133, respectively. Sealing sticker 160A seals closure panels 154A and 154B in the closed position so that blinded trial product 158 cannot be accessed or otherwise tampered with without tearing one of sealing sticker 160. It is appreciated that one, two, three, four or more sealing stickers 152 can be placed at spaced apart locations between closure panels 154A and/or 154B and corresponding panels 132 and 133.

Sealing stickers 160 each comprise an outer layer 162 that is typically comprised of a layer of paper, plastic, metal foil, or another sheet material or composite. Outer layer 162 has an exterior surface 163 and an opposing interior surface 164. A layer of adhesive is applied on interior surface 164 for adhering sealing sticker 160 to packaging box 12. Sealing stickers 160 can have a variety of different sizes, shapes, colors, and material composition. For example, sealing sticker 160 could be square, rectangular, round, elliptical, star shaped, polygonal, have an irregular configuration or have other shapes. Furthermore, a variety of different markings, designs, or other indicia such as bar codes or other identifying indicia can be printed, embossed, affixed or otherwise marked on exterior surface 163 to assist in identifying sealing stickers 160.

In the depicted embodiment, sealing stickers 160 are placed at a perimeter edge or corner of packaging box 12. However, in other embodiments, end closures 142 and 144 could be formed from two, three, four or more panels that extend from the terminal edge of two or more of panels 132-135. These panels can either intersect or overlap centrally over openings 150A or 150B so that one or more sealing stickers 160 extend between two or more of the panels at a central location of end closures 142/144, i.e., inwardly spaced apart from the perimeter edge. In this case, sealing stickers 160 may only extend substantially flat as opposed to bending around a corner. In still other embodiments, portions of end closures 142/144 may extend over the exterior surface of panel 132-135 so that when sealing stickers 160 extend between end closures 142/144 and one or more of panels 132-135, sealing stickers 160 only extend substantially flat. In view of the foregoing, depending on the configuration of packaging box 12, any number of sealing stickers 160 may be used and they may be placed at any desired location on packaging box 12 for sealing packaging box 12 closed. Other examples of packaging boxes 12 and how sealing stickers 160 can be applied thereto are disclosed in U.S. Provisional Application No. 62/412,008, filed Oct. 24, 2016, which is incorporated herein by specific reference.

Figure 7:
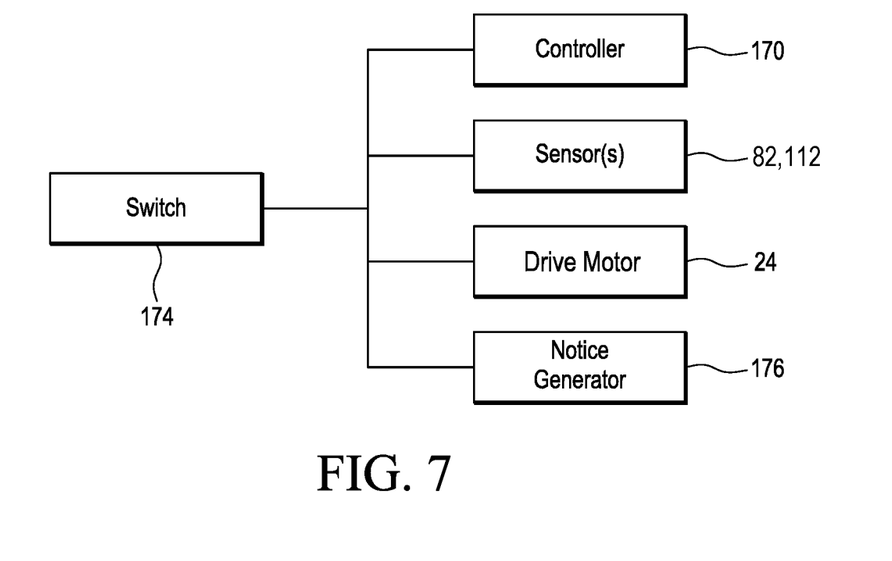
FIG. 7 is a schematic representation of the electronics of the tamper seal detection system shown in FIG. 1.
Figure 7A:
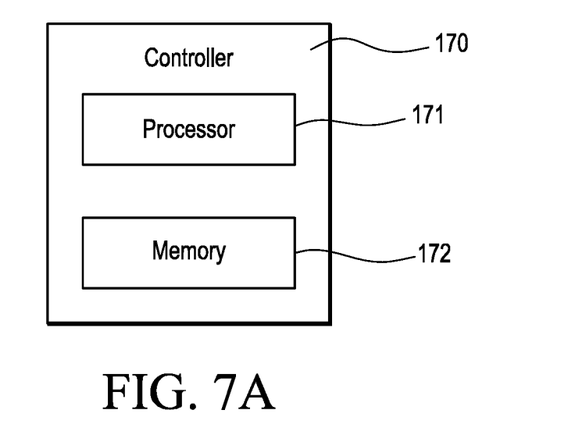
FIG. 7A is a schematic representation of one embodiment of the controller shown in FIG. 7.

Depicted in FIG. 7 is a schematic representation of one example of electronics that can be used in association with tamper seal detection system 10. The electronics include an electronic controller 170. Controller 170 comprises a programmable logic controller (PLC) or other types of computers. In other embodiments, as depicted in FIG. 7A, controller 170 can comprise a computer processor 171 that operates in conjunction with computer memory 172, such as non-transitory memory. A PLC can also operate in conjunction with separate memory 172. Other types of electronic controllers that can perform the functions discussed herein can also be used. Controller 170 can be either preprogrammed, such as by being hardwired, or can be operated by executing executable code loaded within memory to perform the functions discussed herein. Memory 172 can also be used for storing data generated from sensors 82 and/or 112. Also electrically coupled with controller 170 are the one or more sensors 82 and 112 and drive motor 24. As discussed below in greater detail, a notice generator 176 can be electrically coupled with controller 170 for generating desired notice signals, such as light or sound. A manual or automatic switch 174 is electrically coupled with controller 170 and can be used for activating the system.

The process of using tamper seal detection system 10 with packaging boxes 12 will now be described. Initially, packaging boxes 12 (FIGS. 3 and 4) are typically provided in a flat collapsed state. An operator will then fold the collapsed box into an erected three-dimensional configuration so that at least one of openings 150 remains open. In other embodiments, packaging boxes 12 may be provided to the operator in a partially erected state. A desired blinded trial product 158 is then positioned within compartment 148 of packaging box 12 following which closure panels 154A and 154B are moved to the closed position so that the blinded trial products 158 is enclosed within packaging box 12.

Next, the desired number of sealing stickers 160 are then placed on packaging box 12 so that packaging box 12 is sealed closed, i.e., the blinded trial products 150 within packaging box 12 cannot be accessed without tearing a sealing sticker 160. Often the number of sealing stickers 160 necessary to effectively seal packaging box 12 is two, i.e., one sticker for each closure panel 154A and 154B, as discussed above. However, depending on the size, shape and configuration of packaging box 12, other numbers of sealing stickers 160 may be needed or can be used to effectively seal packaging box 12 closed. For example, in one embodiment only one sealing sticker 160 may be required while in other embodiments three, four, five, or more sealing stickers 160 may be required.

Figure 5:
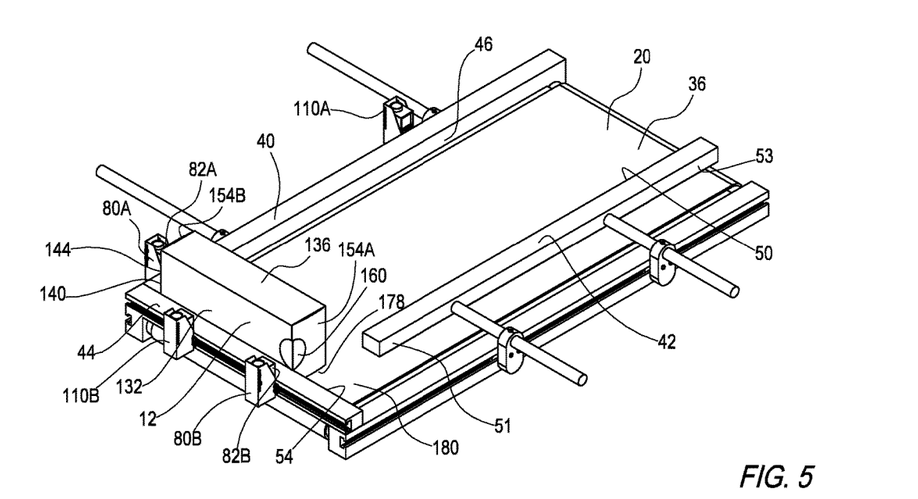
FIG. 5 is a perspective view of the tamper seal detection system shown in FIG. 1 with the packaging box in a first position.

Prior to or after packaging box 12 is sealed closed, tamper seal detection system 10 is adjusted to properly receive packaging box 12 and detect sealing stickers 160. Specifically, as depicted in FIG. 5, guide rails 40 and 44 can be adjusted, if needed, as previously discussed, so that packaging box 12 can be placed on top surface 36 of conveyor belt 20 with end 140 of packaging box 12 abutting inside face 46 of first side guide rail 40 and the side wall 136 of packaging box 12 abutting inside face 54 of rear guide rail 44. More specifically, guide rails 40 and 44 are positioned so that closure panel 154B or end closure 144 can be butted against first side guide rail 40 and front panel 132 can be butted against rear guide rail 44. The orientation of packaging box 12 can change depending on the configuration and size of packaging box 12 and the location of sealing stickers 160. By using guide rails 40 and 44 guides, each packaging box 12 can always be set at the same location and in the same orientation on conveyor belt 20. The area of conveyor belt 20 adjacent to guide rails 40 and 44 on which packaging box 12 sits during sensing by sensors 82 is herein referred to as inspection zone 178.

Prior to operation of tamper seal detection system 10, second side guide rail 42 is also properly positioned. As discussed below in more detail, once a packaging box 12 has been approved, conveyor belt 20 is activated to move packaging box 12 forward and thus make room for the next packaging box 12 to be placed in inspection zone 178. Second side guide rail 42 is positioned to help guide packaging box 12 as packaging box 12 travels along the length of conveyor belt 20. As such, inside face 50 of second side guide rail 42 is positioned to be disposed adjacent to end 138, and more specifically, closure panel 154A of packaging box12 as shown in FIG. 6.

It is noted that in the embodiment depicted in FIG. 5 that end 51 of second side guide rail 42 is spaced apart from, i.e., spaced forward of, rear guide rail 44 so that an access opening 180 is formed between second side guide rail 42 and rear guide rail 44. In one method of use, packaging boxes 12 can be positioned in inspection zone 178 by being laterally slid through access opening 180 and onto conveyor belt 20. For example, a table or other support structure can be disposed adjacent to conveyor belt system 14 having a top surface that is substantially flush with top surface 36 of conveyor belt 20. An operator can then manually slide packaging boxes 12 through access opening 180 and into inspection zone 178 using rear guide rail 44 has a constant guide. Alternatively, a mechanical arm or other mechanism can be use to automatically or selectively push packaging boxes 12 through access opening 180 and into inspection zone 178, again using rear guide rail 44. This configuration has the benefit that packaging boxes 12 never need to be vertically picked up to be placed within inspection zone 178. However, in other embodiments, access opening 180 can be eliminated and each packaging box 12 can be manually or mechanically picked up and placed in inspection zone 178.

With guide rails 40 and 44 properly positioned, sensor assemblies 80A and 80B can be adjusted vertically and horizontally, as previously discussed, so that when packaging box 12 for a set configuration is disposed within inspection zone 178 against guide rails 40 and 44, sensors 82A and 82B are sufficiently aligned with corresponding sealing stickers 160A and 160B so that sealing stickers 160A and 160B can be detected by sensors 82A and 82B. Sensors 82 can be horizontally aligned with a corresponding sealing sticker 160 or angled so as to be directed to a sealing sticker 160. Depending on the proximity of sealing stickers 160, a single optical sensor 82 may be sufficient to detect two or more sealing stickers 160. Otherwise, additional sensors 82 will need to be added and properly adjusted so as to be sufficiently aligned with the other sealing stickers 160.

Controller 170 is programmed to determine whether the area visually inspected by optical sensor 82 contains a sealing sticker 160. This is typically accomplished by controller 170 determining whether the area visually inspected by optical sensor 82 contains an object having a size, shape, color, markings, and/or other predefined characteristics that match corresponding pre-programmed characteristics of sealing sticker 160. Other programming methods can also be used. Accordingly, optical sensors 82 can also be used to discern between sealing stickers having different size, shape, color, markings, and/or other predefined characteristics.

In addition to or in place of the foregoing, controller 170 acting with sensors 82 can also be programed to detect if sealing stickers 160 are in a desired orientation or location. For example, to ensure that there is no differentiation between packaging boxes 12 which could influence the blinded testing, it can be desired that all sealing stickers 160 be placed at the exact same location on each packaging 12 within a predefined tolerance, i.e., each sealing sticker 160 be placed within the same predefined area of each packaging box 12. Likewise, where sealing stickers 160 are non-symmetrical or have non-symmetrical indicia thereon, it can be desired that all sealing stickers 160 are placed at the same orientation within a predefined tolerance, thereby again ensuring no differentiation between packaging boxes 12. Controller 170 acting with sensors 82 can be programmed to determine if sealing stickers 160 that are being detected satisfy the location and/or orientation requirements. Controller 170 can also be used to count and record the number and type of sealing stickers 160 located on each specific packaging box 12.

Prior to operation, sensor assemblies 110A and 110B can be adjusted vertically and/or horizontally to be properly positioned. Sensor assembly 110A is disposed toward second end 34 of conveyor belt system 14 and optical sensor 112A thereof is orientated so that it can detect when a packaging box 12 traveling on conveyor belt 20 passes optical sensor 112A. As discussed below, this sensing can be used to control movement of conveyor belt 20 during the inspection process.

Sensor assembly 110B is disposed on rear guide rail 44 and optical sensor 112B thereof is orientated so that it can detect when a packaging box 12 is disposed within inspection zone 178. Thus, in one embodiment, optical sensor 112B can function as switch 174 (FIG. 7) to activate tamper seal detection system 10 when a packaging box 12 is detected.

Once the sensors and guide rails of tamper seal detection system 10 are adjusted, a switch can be activated putting tamper seal detection system 10 in a ready mode. In the ready mode, notice generator 176 (FIG. 7) can send signals indicating whether the sensors are ready for operation. For example, light sources 86 (FIG. 6) of each sensor assembly can produce a signal, such as by flashing or emitting a specific light color, to identify operating conditions such as whether sensors 82 and/or 112 are obstructed, incorrectly positioned or incorrectly adjusted. If the conditions of the ready mode are satisfied, a sealed packaging box 12 is manually or automatically placed in inspection zone 178 so as to rest on conveyor belt 20 and butt against guide rails 40 and 44. As discussed above, this can be accomplished by sliding packaging box 12 through access opening 180 or by picking up packaging box 12 and placing it in inspection zone 178. As packaging box 12 enters inspection zone 178, packaging box 12 is sensed by sensor 112B which, through controller 170, activates sensors 82A and 82B to optically sense or inspect defined areas on packaging box 12 and detect whether the sealing stickers 160A and 160B are present in the desired locations, i.e., controller 170 determines whether the pre-program sealing sticker characteristics are present. If desired, sensor 112B could be replaced by a manual switch or some other automated switch.

Controller 170 with sensors 82 can detect whether the desired number of sealing stickers 160 are present on packaging box 12 and if they are at desired locations. In addition, each packaging box 12 could include a unique identifier, such as a bar code, printed indicia or other identifier, that is disposed directly on the packaging box 12 or on a sealing sticker 160 or other sticker placed on packaging box 12. Sensors 82 or other types of scanners or sensors could then be used to record that the specific packaging box 12 was scanned and also record data detected from the scan, i.e., record the number, type, placement, orientation, color, configuration and/or other characteristics of sealing stickers 160 or other stickers or indicia on packaging box 12.

If it is determined that packaging box 12 satisfies predefined conditions, i.e., the proper number and/or type of sealing stickers 160 are located on packaging box 12 at the desired locations and/or orientations, controller 170 can control drive motor 24 so as to cause conveyor belt 20 to move a predetermined distance so that the inspected packaging box 12 is out of inspection zone 178, thereby permitting a new packaging box 12 to be placed in the inspection zone 178. This positive result may also be accompanied by notice generator 176 emitting a notice signal such activating light source 86 or a sound generator. For example, light source 86 may glow green or some other predefined color if the sealing stickers 160 are detected. If it is determined that the packaging box 12 does not satisfy the predefined conditions, controller 170 will not move conveyor belt 20 and notice generator 176 may generate a separate notice signal, such as a separate sound, light, or other indication, that designates failure. In this case, the operator is required to remove packaging box 12 from inspection zone 178 so that the packaging box 12 can then be visually inspected to determine the cause of the failure. The next packaging box 12 can then be placed within inspection zone 178 and the process repeated. By having a separate light source 86 associated with each optical sensor 82, light sources 86 can be used to identify which sealing stickers 160 are missing or incorrectly positioned.

Optical sensor 112A functions as a packaging backup sensor. That is, as each packaging box 12 is inspected and approved, conveyor belt 20 moves the packaging boxes 12 downstream at staggered intervals. As long as packaging boxes 12 continue to pass optical sensor 112A, tamper seal detection system 10 continues to run as normal. However, if packaging boxes 12 begin to gather and build up at second end 34 of conveyor belt 20, optical sensor 112A will eventually detect that packaging boxes 12 are staying fixed in front of optical sensor 112A and will thus shut down operation of tamper seal detection system 10.

In view of the foregoing, tamper seal detection system 10 provides a number of unique advantages. For example, detection system 10 helps to reduce or eliminate human error in the inspection process by requiring a highly accurate, computer controlled inspection of each packaging box. Furthermore, the detection system 10 can automatically maintain an ongoing record of the inspection process that enables an operator to easily verify the inspection process. In addition, the inspection process is performed in real time. That is, each packaging box is approved as it is inspected. As such, it should never be necessary to re-inspect all of the sealed packaging boxes based on a missing sealing sticker or miscounted stickers. Other benefits also exist.

Figure 8:
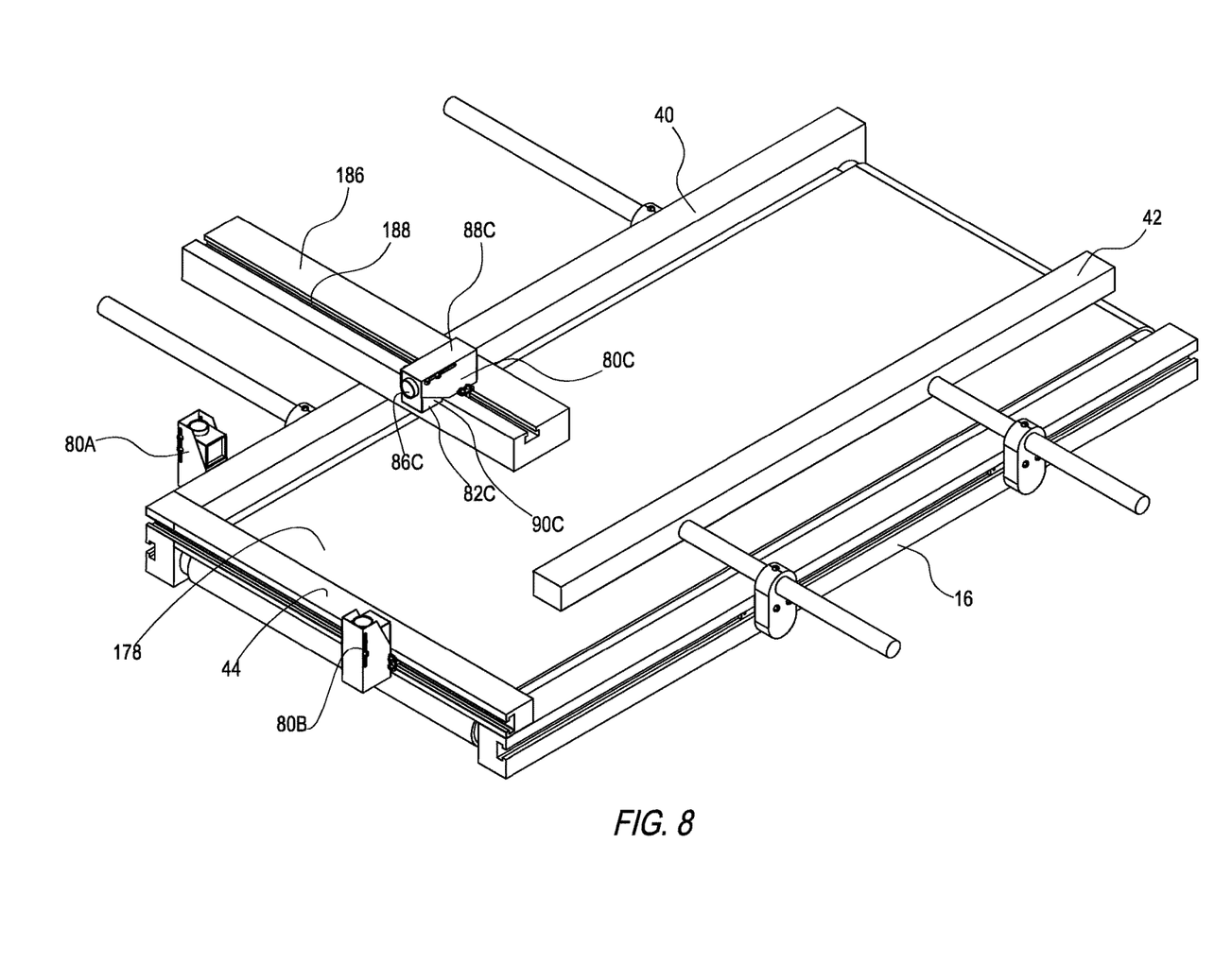
FIG. 8 is a perspective view of an alternative embodiment the tamper seal detection system shown in FIG. 1.

Depicted in FIG. 8 is a tamper seal detection system 10A incorporation features of the present invention. Tamper seal detection system 10A is substantially the same as tamper seal detection system 10 and thus like elements between systems 10 and 10A are identified by like reference characters. The only difference between system 10 and 10A is that system 10A also includes an optical sensor assembly 80C disposed vertically above conveyor belt 20 having an optical sensor 82C that is directed to inspection zone 178 so that optical sensor 82C can further inspect sealing stickers 160 on packaging boxes 12 within inspections zone 178. That is, depending on the shape the packaging box 12, sealing stickers 160 can be placed at a variety of different locations. In some embodiments, optical sensor 82C may be needed to detect a sealing sticker that cannot be detected by optical sensors 82A or 82B.

Sensor assembly 80C has the same configuration and elements as sensor assemblies 80A and 80B and thus like elements are identified by like reference characters except that the elements of sensor assembly 80 are associated with the letter "C." Sensor assembly 80C is retained on an upper rail 186 having a T-shaped slot extending along the length there. Sensor assembly 80C in retained on rail 186 in the same manner as sensors assembly 80A is retained on first side guide rail 40. As such, optical sensor 82C can also be selectively adjusted in two directions.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for detecting sealing stickers on a packaging box, the method comprising:
    placing a first packaging box onto a conveyor belt of a conveyor belt system at an inspection zone, the first packaging box having a first sealing sticker thereon that at least partially seals the first packaging box closed;
    activating a first optical sensor to detect whether the first sealing sticker is located on a first side of the first packaging box while the packaging box is in the inspection zone; and
    automatically moving the conveyor belt of the conveyor belt system a predefined distance so that the first packaging box is moved out of the inspection zone if the first optical sensor detects that the first sealing sticker is located on the first side of the first packaging box.

2. The method as recited in claim 1, further comprising not moving the conveyor belt of the conveyor belt system if the first optical sensor detects that the first sealing sticker is not located on the first side of the first packaging box until after the first packaging box is removed from the conveyor belt.

3. The method as recited in claim 1, further comprising placing a first packaging box onto the conveyor belt so that that first packaging box butts against a rear guide rail and butts against a side guide rail.

4. The method as recited in claim 1, further comprising placing a second packaging box on the conveyor belt in the inspection zone after the conveyor belt has moved the predefined distance.

5. The method as recited in claim 1, wherein prior to the step of inserting the first packaging box the method comprises:
    inserting a blinded trial product into a compartment of the first packaging box;
    folding the first packaging box into a closed position; and
    applying the first sealing sticker to the packaging box so as to at least partially seal the packaging box closed.

6. The method as recited in claim 1, further comprising manually adjusting the position of the first optical sensor before placing a first packaging box onto the conveyor belt.

7. The method as recited in claim 1, wherein an electronic controller is in electrical communication with the first optical sensor, the electronic controller being programed to generate a notice signal when the first optical sensor detects that the first sealing sticker is located on a first side of the first packaging box.

8. The method as recited in claim 1, wherein the first optical sensor detects the first sealing sticker based on the color, size, shape, or orientation of the first sealing sticker or indicia disposed on the first sealing sticker.

9. The method as recited in claim 1, wherein the first optical sensor detects whether the first sealing sticker is located within a specific predefined area on the first side of the packaging box.

10. The method as recited in claim 1, wherein the first optical sensor is a luminescence sensor.

11. The method as recited in claim 1, further comprising activating a first proximity sensor to detect whether the first packing box is in the inspection zone.

12. The method as recited in claim 1, wherein the step of placing the first packaging box onto the conveyor belt comprises:
    adjusting a lateral position of a second side guide rail; and
    placing the first packaging box onto the conveyor belt so that the packing box is disposed between a first side guide rail and the second side guide rail.

13. A tamper seal detection system for detecting a sealing sticker on a packaging box, the system comprising:

a conveyor belt system having a movable conveyor belt with an inspection zone that is configured to receive a packaging box having one or more sealing stickers thereon;

a rear guide rail and a first side guide rail disposed adjacent to the conveyor belt of the conveyor belt system; and a first sensor secured to the rear guide rail or the first side guide rail and being configured to detect the presence of a first sealing sticker located on the packaging box when the packaging box is received on the conveyor belt within the inspection zone.

14. The tamper seal detection system as recited in claim 13, further comprising a second sensor secured to the other of the rear guide rail or the first side guide rail and being configured to detect the presence of a second sealing sticker located on the packaging box when the packaging box is received on the conveyor belt within the inspection zone.

15. The tamper seal detection system as recited in claim 13, wherein the first sensor is adjustable mounted on the housing so that the first sensor can be moved in at least two dimensions.

16. The tamper seal detection system as recited in claim 13, further comprising a second side guide rail that is disposed parallel to the first side guide rail and can be moved laterally.

17. The tamper seal detection system as recited in claim 13, further comprising an electronic controller in electrical communication with the conveyor belt system and the first sensor.

18. The tamper seal detection system as recited in claim 17, further comprising a notice generator in electrical communication with the electronic controller.

19. The tamper seal detection system as recited in claim 13, further comprising:

an electronic controller in electrical communication with the conveyor belt system and the first sensor, the electronic controller being programmed to perform the following functions:

activating the first sensor to determine whether the first sealing sticker is located on a first side of the packaging box that is located within the inspection zone; and sending a signal to the conveyor belt system which causes the conveyor belt system to move the conveyor belt a predetermined distance.

20. The tamper seal detection system as recited in claim 13, further comprising a first proximity sensor disposed on the rear guide rail or the first side guide rail, the proximity sensor being capable of detecting whether a packaging box is located within the inspection zone.

21. A method for detecting sealing stickers on a packaging box, the method comprising:

placing a first packaging box onto a conveyor belt of a conveyor belt system at an inspection zone, the first packaging box having a first sealing sticker thereon that at least partially seals the first packaging box closed; and activating a first optical sensor to detect whether the first sealing sticker is located on a first side of the first packaging box while the packaging box is in the inspection zone, wherein an electronic controller is in electrical communication with the first optical sensor, the electronic controller being programed to generate a notice signal when the first optical sensor detects that the first sealing sticker is located on a first side of the first packaging box.

22. A method for detecting sealing stickers on a packaging box, the method comprising:

placing a first packaging box onto a conveyor belt of a conveyor belt system at an inspection zone, the first packaging box having a first sealing sticker thereon that at least partially seals the first packaging box closed; and activating a first optical sensor to detect whether the first sealing sticker is located on a first side of the first packaging box while the packaging box is in the inspection zone, the first optical sensor detecting the first sealing sticker based on the color, size, shape, or orientation of the first sealing sticker or indicia disposed on the first sealing sticker.

23. A method for detecting sealing stickers on a packaging box, the method comprising:

placing a first packaging box onto a conveyor belt of a conveyor belt system at an inspection zone, the first packaging box having a first sealing sticker thereon that at least partially seals the first packaging box closed;

activating a first proximity sensor to detect whether the first packing box is in the inspection zone; and activating a first optical sensor to detect whether the first sealing sticker is located on a first side of the first packaging box while the packaging box is in the inspection zone.

* * * * *